United States Patent
Cotarca et al.

(10) Patent No.: US 7,393,975 B2
(45) Date of Patent: *Jul. 1, 2008

(54) PROCESS FOR THE PURIFICATION OF GABAPENTIN

(75) Inventors: Livius Cotarca, Cervignano del Friuli (IT); Roberto Giovanetti, Schio (IT); Andrea Nicoli, Vicenza (IT)

(73) Assignee: ZACH System S.p.A., Bresso (IT)

( * ) Notice: Subject to any disclaimer, the term of this patent is extended or adjusted under 35 U.S.C. 154(b) by 329 days.

This patent is subject to a terminal disclaimer.

(21) Appl. No.: 10/561,018

(22) PCT Filed: Jun. 17, 2004

(86) PCT No.: PCT/EP2004/006513

§ 371 (c)(1),
(2), (4) Date: Dec. 16, 2005

(87) PCT Pub. No.: WO2004/113269

PCT Pub. Date: Dec. 29, 2004

(65) Prior Publication Data

US 2007/0129569 A1    Jun. 7, 2007

(30) Foreign Application Priority Data

Jun. 20, 2003   (IT)   ............ MI2003A1247

(51) Int. Cl.
*C07C 61/08*   (2006.01)

(52) U.S. Cl. .................................... 562/507
(58) Field of Classification Search ............ 562/504
See application file for complete search history.

(56) References Cited

U.S. PATENT DOCUMENTS

| | | | | |
|---|---|---|---|---|
| 5,279,744 A | * | 1/1994 | Itoh et al. | ............ 210/676 |
| 6,054,482 A | * | 4/2000 | Augart et al. | ............ 514/561 |
| 2007/0129569 A1 | | 6/2007 | Cotarca et al. | |

FOREIGN PATENT DOCUMENTS

| | | |
|---|---|---|
| EP | 0 414 263 | 2/1991 |
| WO | 00/01660 | 1/2000 |
| WO | 02/34709 | 5/2002 |

OTHER PUBLICATIONS

U.S. Appl. No. 10/582,790, filed Jun. 14, 2006, Giovanetti et al.
U.S. Appl. No. 10/561,018, filed Dec. 16, 2005, Cotarca et al.
U.S. Appl. No. 10/593,813, filed Sep. 22, 2006, Giovanetti et al.
U.S. Appl. No. 11/722,056, filed Jun. 18, 2007, Giovanetti et al.

* cited by examiner

*Primary Examiner*—Karl J Puttlitz
(74) *Attorney, Agent, or Firm*—Oblon, Spivak, McClelland, Maier & Neustadt, P.C.

(57) ABSTRACT

A process for the preparation of gabapentin which comprises the passage of a gabapentin inorganic salt through a strong cationic ionic exchange resin, the elution of gabapentin fixed on the column, the concentration of the resultant solution and the cristallization from organic solvent, characterized in that the elution of gabapentin fixed on the column is carried out by using an ammonia and alkaline hydroxide aqueous solution, is described.

5 Claims, No Drawings

PROCESS FOR THE PURIFICATION OF GABAPENTIN

The present invention relates to a process for the preparation of gabapentin.

Gabapentin (The Merck Index XII Ed., page 733, No. 4343) is a known drug endowed with anti-epileptic activity described for the first time by Warner Lambert Co. in the U.S. Pat. No. 4,024,175.

In the literature several processes for the preparation of gabapentin are reported (see for example the U.S. Pat. Nos. 4,024,175, 5,068,413 and 5,091,567).

Substantially, all these methods foresee a final step of purification by column chromatography of an aqueous solution of a gabapentin salt, generally hydrochloride, through a weak basic ionic exchange resin.

In the patent application PCT No. WO 02/34709 in the name of the same Applicant, a process of purification that foresees the chromatography of an aqueous solution of gabapentin hydrochloride through strong cationic ionic exchange resins is described.

The process described in the above cited PCT patent application is very efficient and it allows to obtain, after concentration of the eluate and crystallization, a high pure product, almost completely free from the corresponding lactam which is a substance endowed with a certain toxicity (Von A. Enders et al., Arzneimittel Forschung, 10, (1960), 243-250).

During the chromatographic phase on cationic resin, gabapentin is fixed to the resin allowing the other substances to percolate, in particular organic impurities coming from the synthetic process.

Gabapentin is then eluted with an ammonia aqueous solution with a concentration around 3-4% and then with water.

The fractions containing gabapentin are collected and concentrated under vacuum till obtaining a solid residue from which gabapentin is isolated by crystallization from organic solvents, preferably alcoholic solvents.

The above described process itself appears [to be] optimum with regard to the purification of gabapentin.

Nevertheless, said process needs a high amount of ammonia solution (about 4500 liters at 3% for 350 Kg of gabapentin). The ammonia solution must then be drained by a biological draining system and this results both in an increase in costs and in a prolonged utilization of the draining system itself.

We have now found a variation to the process described in the patent application PCT No. WO 02/34709 which allows to considerably reduce the amount of the used ammonia solution obtaining at the same time an equally pure product and with substantially the same yields. Said variation consists in eluting gabapentin fixed on the strong cationic resin with an ammonia and alkaline hydroxyde aqueous solution.

Therefore, object of the present invention is a process for the preparation of gabapentin which comprises the passage of a gabapentin inorganic salt through a strong cationic ionic exchange resin, the elution of gabapentin fixed on the column, the concentration of the resultant solution and the crystallization from organic solvent, characterized by the fact that the elution of gabapentin fixed on the column is carried out by using an ammonia and alkaline hydroxide aqueous solution.

Preferably, for economic reasons purely, the alkaline hydroxide is sodium hydroxide.

Not limitative examples of strong cationic resins useful in the process of the invention are IRA120, DIAION SK1B and IMAC HP1110.

The amount of alkaline hydroxide must not exceed the molar amount of cationic resin used in order to minimize the amount of alkaline hydroxide which elutes with gabapentin forming an alkaline salt of gabapentin.

Preferably, the concentration of $NH_3$ in the elution solutions is around 3-4% by weight and the concentration of NaOH around 7% by weight. The ratio between $NH_3$ and NaOH is preferably from 1:1 to 1:2.

At the end of elution the column is washed with demineralised water.

Practically, the method object of the invention allows to substitute a relevant amount (about 60-70%) of ammonia with sodium hydroxide and this results in a significant reduction of draining time and costs of the ammonia solution.

As further collateral advantage, the eluate volume is reduced of about 20% with further reduction of costs and time.

Thus, for example, if 4500 l of an aqueous solution of $NH_3$ at 3% every 350 Kg of gabapentin by the method described in the patent application PCT No. WO 02/34709 were necessary, 4100 l of an aqueous solution of $NH_3$ at 3% (1400 l) and a solution of NaOH at 7% (2700 l) for the same amount of gabapentin by the method object of the present invention are sufficient.

The eluate also contains a small amount of alkaline hydroxide in the form of gabapentin salt, for example sodium salt, which may possess a destabilizing effect on gabapentin.

Nevertheless, the elimination of the sodium salt can be realized by adding a small amount of mineral acid to the solution, preferably HCl.

HCl (a diluted aqueous solution) can be directly added in the eluate or after having concentrated it at about 50% by distillation i.e. after having substantially removed the ammonia.

The subsequent crystallization according to known techniques removes a great part of the chlorides added, giving gabapentin containing chlorides between 30 and 70 ppm i.e. in line with pharmacopoeia requirements (less than 100 ppm).

In a practical embodiment the process of the invention comprises fixing gabapentin on a strong cationic resin, washing with water in order to remove the inorganic acid, eluting the resin with an ammonia and sodium hydroxide aqueous solution and washing the resin with demineralised water, collecting the fractions containing gabapentin, concentrating the solution till about 50%, neutralizing the present sodium salt of gabapentin with HCl, further concentrating till obtaining a thick residue, crystallizing gabapentin from alcoholic solvents. For better illustrating the present invention the following examples are now given.

EXAMPLE 1

In a glass column (diameter 45 mm, height 450 mm) endowed with porous septum, 500 ml of suitably activated and regenerated resin Diaion SK1B were charged.

A solution of gabapentin hydrochloride (652 g of solution at 14.48% equal to 94.4 g of gabapentin) was eluted through the column.

The column was then washed eluting with demineralised water about 1500 g till pH 7.

Then, a mixture (720 g) of an ammonia solution at 3% (240 g) and a solution of NaOH at 7% (480 g) was eluted through the column.

At the end the column was eluted with demineralised water till pH 7 (about 1500 g).

The fractions of eluate containing gabapentin were collected obtaining a solution (2171 g) containing gabapentin (4.25%, 92.3 g).

To the solution, 23.4 g of HCl solution at 3.99% (equal to 0.934 g of HCl) was added.

The solution was then concentrated under vacuum at a temperature below 40° C. obtaining a crude (91.2 g) containing gabapentin at 97.6%.

In a 500 ml reactor under nitrogen crude gabapentin (70 g), demineralised water (34.7 g) and methanol (43.7 g) were charged.

The suspension was heated at 50° C. for 30 minutes and then isopropyl alcohol (180.5 g) was added dropwise in 30 minutes.

The mixture was kept at 50° C. for further 30 minutes and then it was cooled at 25° C. in 2 hours and at −5° C. in a further hour, keeping this temperature for further 2 hours.

The solid was filtered and washed on the filter with isopropyl alcohol cooled at −5° C.

After drying in oven at 45° C., gabapentin (64 g) was obtained with purity higher than 99%, lactam under 0.01% and 69 ppm of chlorides (expressed as Cl$^-$).

The invention claimed is:

1. A process for the preparation of gabapentin which comprises the passage of a gabapentin inorganic salt through a strong cationic ionic exchange resin, the elution of gabapentin fixed on the column, the concentration of the resultant solution and the cristallization from organic solvent, characterized in that the elution of gabapentin fixed on the column is carried out by using an ammonia and alkaline hydroxide aqueous solution.

2. A process according to claim 1 wherein the alkaline hydroxide is NaOH.

3. A process according to claim 1 wherein the ammonia and NaOH aqueous solution is obtained by mixing an ammonia aqueous solution at 3-4% with a sodium hydroxide aqueous solution at 7-8%.

4. A process according to claim 1 wherein the gabapentin sodium salt that is present in the eluate is neutralized with an aqueous solution of HCl.

5. A process according to claim 1 which comprises fixing gabapentin on a strong cationic resin, washing with water, eluting the resin with an ammonia and sodium hydroxide aqueous solution and washing the resin with demineralised water, collecting the fractions containing gabapentin, concentrating the solution till about 50%, neutralizing by HCl the present gabapentin sodium salt, further concentrating till a thick residue, crystallizing gabapentin from alcoholic solvents.

* * * * *